United States Patent [19]

Debat et al.

[11] 4,235,890

[45] Nov. 25, 1980

[54] *STEPHANIA CEPHARANTHA* EXTRACT, ITS METHOD OF PREPARATION AND ITS USE AS PHARMACEUTICAL

[75] Inventors: Jacques Debat, Saint Cloud; Jean Lemoine, Garches; Françoise Lier nee Gabillault Plaisir, all of France

[73] Assignee: Laboratoire Debat, Paris, France

[21] Appl. No.: 44,313

[22] Filed: May 31, 1979

[30] Foreign Application Priority Data

May 31, 1978 [GB] United Kingdom ............... 25618/78

[51] Int. Cl.³ .......................... A01N 9/02; A01N 9/08
[52] U.S. Cl. .................................................. 424/195
[58] Field of Search ........................................ 424/195

[56] References Cited

PUBLICATIONS

Chemical Abstracts, (1976) vol. 85 No. 17, 135(a).

*Primary Examiner*—Elbert L. Roberts
*Attorney, Agent, or Firm*—Bacon & Thomas

[57] ABSTRACT

This invention is concerned with the preparation of an extract of *Stephania cepharantha* which is useful in therapy, in particular as bacteriostatic and antiphlogistic and antalgic agent.

A therapeutical composition is proposed which contains, in association with a physiologically acceptable excipient, a pharmaceutically effective amount of said *Stephania cepharantha* extract.

7 Claims, No Drawings

STEPHANIA CEPHARANTHA EXTRACT, ITS METHOD OF PREPARATION AND ITS USE AS PHARMACEUTICAL

BACKGROUND OF THE INVENTION AND PRIOR ART

*Stephania cepharantha* is a plant of the Menispermaceae family which grows in China and Japan. It has been disclosed by R. R. PARIS and H. MOYSE in "Matière Médicale" vol. 2, page 178 (Masson ed., Paris 1967).

It is also known, in particular from the R. R. PARIS and H. MOYSE publication, that root extracts of *Stephania cepharantha* prepared by extraction with a water-alcohol mixture [such as a water-ethanol (50:50) v/v mixture] at 60°–100° C., have been proposed in folk medicine in the treatment of tuberculosis and leprosis.

It has now been found that the stem extract of Stephania cepharanthais (i) different from the previous root extracts of the very same plant, and (ii) useful in therapy, in particular in the treatment of infectious diseases in view of its bacteriostatic, antalgic and antiphlogistic properties.

SUBJECT OF THE INVENTION

The subject of the invention is to propose a method of extraction of stems of *Stephania cepharantha* in order to obtain a new extract which is useful in the treatment of human beings suffering, in particular from infectious diseases.

DETAILED DESCRIPTION OF THE INVENTION

According to the present invention the stems of the plant are extracted with at least one solvent. The product thus obtained is then purified, if necessary, and then recovered according to a method known per se.

The extraction can be carried out by using, per liter of solvent, 30 to 150 g of ground dry plant, Solvents which can be used include water, alcohols (such as methanol, ethanol, propanol and isopropanol), ketones (such as acetone, methyl ethyl ketone and methyl propyl ketone), ethers (such as dimethyl ether, diethyl ether and diisopropyl ethyl), esters (such as ethyl acetate), hydrocarbons (such as pentane, hexane, cyclopentane, cyclohexane, petroleum ether and benzene), halogenated hydrocarbons (such as chloroform and methylene chloride), and mixtures thereof.

BEST MODE

The preferred solvents in order to extract the *Stephania cepharantha* stems are chloroform, methanol and a methanol-water (75:25) v/v mixture.

The extract, which is obtained by extraction of one solvent then evaporation to dryness under reduced pressure, generally contains alkaloid components and non-alkaloid components. The preferred methods for recovering the alkaloids are given in examples 2 and 3 hereinafter, the method of example 3 enabling to isolate both the alkaloid and non-alkaloid components.

EXAMPLE 1

Preparation of the total extract 140 g of ground and dried stems of *Stephania cepharantha* are extracted with 3 liters of methanol in a Soxhlet apparatus for 4 hours. The insoluble material is discarded and the methanol solution is evaporated to dryness under reduced pressure to obtain a dry product which is taken up in the minimal amount of water and then lyophilised. 85 g of total extract (which is coded as AJ-01) are obtained. The yield is 42.5% by weight with respect to the starting plant material.

EXAMPLE 2

Extraction of the alkaloid components.

(a) Extraction 1.2 kg of dried (at 37° C. in an oven) and ground stems of *Stephania cepharantha* are treated with 1.2 liters of $NH_4OH$ (containing 150 g/liter of $NH_3$) and extracted with 9 liters of $CHCl_3$ in a Soxhlet apparatus. The chloroform solution which is recovered is then concentrated to 3 liters under reduced pressure and extracted with acidulated water (5 times 500 ml of water containing 20 g/liter of citric acid). After adding $NH_4OH$ up to pH8 the free bases contained in the solution are extracted with chloroform (5 times 200 ml). The organical phase is dried over anhydrous sodium sulphate and evaporated to dryness under reduced pressure to give 11.76 g of a dried product called total alkaloid extract. Yield 9.8% by weight with respect to the starting plant material.

(b) Purification

The total alkaloid extract is subjected to an extraction with methanol in a Soxhlet apparatus. The methanol solution is evaporated to dryness under reduced pressure. The evaporation residue is treated with water containing 20 g/l of citric acid and the insoluble is discarded by filtration. $NH_4OH$ is added to the aqueous phase up to pH 8 which is then washed with chloroform (3 times 200 ml). After acidification (with citric acid) the quaternized alkaloids are precipitated by means of the Mayer reagent in order to give, after filtration and drying alkaloid iodomercurates (51 g) which are transformed into chlorides of quaternized alkaloids, by chromatography with an ion exchange resin (Amberlite IRA 400 in the chloride form). After elution and lyophilisation the alkaloid components are obtained.

EXAMPLE 3

Extraction of the alkaloid and non-alkaloid components.

100 g of dried (at 37° C. in an oven) and ground stems of *Stephania cepharantha* are extracted with 1 liter of a boiling methanol-water (75:25) v/v mixture. After filtration of the insoluble, the filtrate is concentrated to 250 $cm^3$ under reduced pressure. The aqueous phase which is obtained is filtered and chromatographied on a non ionic resin (300 ml of Amberlite XAD-2).

The filtrate, which includes the non adsorbed material, is lyophilised. The product thus obtained contains the non-alkaloid components.

Elution of the adsorbed material with an ethanol-water (90:10) v/v mixture gives after concentration (under reduced pressure) then lyophilisation a product containing the alkaloid components.

The extracts of *Stephania cepharantha* according to the invention have been tested with respect to their pharmacological properties. The assays concerning AJ-01 (the extract of example 1) are summed up hereinafter.

(1) Toxicity

AJ-01 administered to animals by i.v. and i.p. routes in solution in physiological serum (water containing 9 g/l of NaCl) is well tolerated. LD-0 (i.e. the maximum non-lethal dose) by i.v. route and i.p. route in mice is higher than 500 mg/kg.

(2) Bacteriostatic activity

AJ-01 exhibits a bacteriostatic activity against gram (+) and gram (−) bacteriae. For instance the MIC (minimal inhibitory concentration) values of AJ-01 are 2 mg/ml on *Staphylococcus aureus* London and 44 mg/ml on a strain of Proteus (Proteus 1557 of the catalogue of the collection of the "Centre International de Distribution de Souches et d'Information sur les Types Microbiens" of Lausanne).

(3) Antiphlogistic activity

The antiphlogistic activity of AJ-01 was studied on female rats (weighing 100 g) according to the carrageen oedema test. The results given in table I for AJ-01 and phenylbutazone (a reference product) show that AJ-01 inhibits in a statistically significant manner the development of the carrageen oedema at 100 mg/kg, the action being maximum 3 hours after administration.

(4) Antalgic activity

The study was carried out according to the method of Koster by i.p. administration to male mice of 0.2 ml of an aqueous solution of acetic acid (30 g/l) 30 minutes after i.p. or oral administration of products (AJ-01 and aspirin as a reference substance) to be tested. The results are given in table II wherein the number of crampings and the percentage variation with respect to the control animals have been given.

The results of the pharmacological assays point out that stems extracts of *Stephania cepharantha* according to the invention such as AJ-01 are useful for the treatment of human beings suffering from infectious diseases, algiae and inflammation.

The invention includes within its scope a therapeutic composition comprising, in association with a physiologically acceptable excipient, a pharmaceutically effective amount of an extract of the invention.

Such a composition can be administered orally in the form of dragees, pills, syrups and potable ampoules, locally in the form of ointments, or sprays or by injection.

TABLE II

ACETIC ACID TEST

| Product (dose) | Number of animals | Number of crampings | Variation with respect to control animals |
|---|---|---|---|
| control | 10 | 28.1 ± 6.8 | — |
| Aspirin 200 mg/kg p.o. | 10 | 17.7 ± 5.0[a] | −37% |
| AJ-01 100 mg/kg i.p. | 10 | 25.0 ± 7.2 | −11% |
| AJ-01 250 mg/kg i.p. | 10 | 19.1 ± 4.0[a] | −32% | note:
[a] statistically significant (p<0.05)

What is claimed is:

1. A method of preparation of an extract of *Stephania cepharantha* useful in therapy which comprises extracting ground dried stems of the plant with at least one solvent selected from the group consisting of water, alcohols, ketones, esters, ethers, hydrocarbons, halogenated hydrocarbons and mixtures thereof.

2. A method of preparation of an extract of *Stephania cepharantha* useful in therapy in particular as bacteriostatic, antiphlogistic and antalgic agent, which comprises extracting 30 to 150 g of ground and dried stems of the plant with 1 liter of a solvent selected from the group consisting of water, alcohols, ethers, esters, ketones, hydrocarbons, halogenated hydrocarbons and mixtures thereof, and recovering said extract by evaporation to dryness of the solution thus obtained under reduced pressure.

3. A method according to claim 2 in which the solvent is selected from the group comprising chloroform, methanol and methanol-water (75:25) v/v mixture.

4. A *Stephania cepharantha* stems extract useful in therapy prepared according to the method of claim 1.

5. A *Stephania cepharantha* stems extract prepared according to the method of claim 2.

6. A *Stephania cepharantha* stems extract prepared according to the method of claim 3.

7. A therapeutical composition useful in the treatment of human beings suffering from infectious diseases, inflammation and algiae comprising in association a physiologically acceptable excipient, a pharmaceutically effective amount of the extract of the stems of *Stephania cepharantha* as defined in claim 4.

* * * * *

TABLE I

CARRAGEEN OEDEMA TEST

| Product (dose) | Number of animals per batch | Plethysmographic measure of oedema volume after administration of carrageen and product to be tested at instant T[a] | | | | |
|---|---|---|---|---|---|---|
| | | T + 1h | T + 2h | T + 3h | T + 4h | T + 5h |
| control | 10 | 4.3 ± 1.3 | 7.2 ± 1.6 | 10.6 ± 2.1 | 12.7 ± 2.2 | 13 ± 1.3 |
| Phenybutazone (20mg/kg) | 8 | 4.6 ± 0.3 (+7%) | 3.8 ± 0.7 (−48%) | 5.2 ± 1.5 (−51%) | 7.2 ± 1.6 (−43%) | 8.3 ± 1.5 (−36%) |
| AJ-01 20 mg/kg) | 10 | 4.0 ± 0.4 (−8% | 5.9 ±1.4 (−18%) | 10.6 ± 1.4 (0%) | 12.7 ±1.1 (0%) | 12.7 ± 1.1 (−2%) |
| AJ-01 (100 mg/kg) | 8 | 3.6 ± 1.6 (−16%) | 5.5 ± 0.8 (−24%) | 7.3 ± 1.9 (−31%)[b] | 10 ± 1.2 (−21%)[b] | 11.5 ± 1 (−12%) |

Notes:
[a] The percentage variation with respect to control animals is given in brackets.
[b] Statistically significant (p<0.05).